US009005543B2

(12) United States Patent
Grenz et al.

(10) Patent No.: US 9,005,543 B2
(45) Date of Patent: Apr. 14, 2015

(54) APPARATUS FOR PUNCHING AND SOLID PHASE EXTRACTION OF DRIED BIOLOGICAL FLUID SPOT AND RELATED METHODS

(75) Inventors: Robert Lee Grenz, Santa Ana, CA (US); William C. Hudson, Tustin, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 456 days.

(21) Appl. No.: 12/917,138

(22) Filed: Nov. 1, 2010

(65) Prior Publication Data

US 2012/0107951 A1 May 3, 2012

(51) Int. Cl.
*B01L 3/02* (2006.01)
*G01N 1/04* (2006.01)
*G01N 1/08* (2006.01)
*G01N 1/40* (2006.01)
*G01N 1/28* (2006.01)
*B01L 3/00* (2006.01)

(52) U.S. Cl.
CPC .............. *G01N 1/286* (2013.01); *B01L 3/0275* (2013.01); *B01L 3/5023* (2013.01); *B01L 2300/0672* (2013.01); *B01L 2300/0681* (2013.01); *G01N 1/405* (2013.01); *G01N 2001/288* (2013.01)

(58) Field of Classification Search
CPC .................. G01N 2001/288; B01L 2300/0672
USPC ............ 422/405, 401, 420, 68.1, 69, 70, 500, 422/501, 519, 527, 534, 535; 436/174, 180, 436/177, 178; 73/61.53, 61.55, 61.59, 73/61.68, 64.56
See application file for complete search history.

(56) References Cited

U.S. PATENT DOCUMENTS

| 4,299,812 | A | 11/1981 | Coombes |
| 4,774,192 | A | 9/1988 | Terminiello et al. |
| 4,816,224 | A | 3/1989 | Vogel et al. |
| 5,204,267 | A | 4/1993 | Sangha et al. |

(Continued)

FOREIGN PATENT DOCUMENTS

| EP | 2447700 A2 | 5/2012 |
| WO | 2010120977 A1 | 10/2010 |

OTHER PUBLICATIONS

European Search Report for EP 11 18 2834-1234 dated Dec. 20, 2012.

(Continued)

*Primary Examiner* — Christopher A Hixson (57) ABSTRACT

An apparatus for punching and extracting analytes from a dried biological fluid spot includes a tube and a sorbent bed. The tube includes a proximal tube opening, a distal tube opening, and a distal section. The distal section includes a tube wall having a tapered diameter that reduces down to the distal tube opening. The apparatus may also include a tube extension that includes an extension wall having a tapered diameter that reduces from a proximal extension opening to a distal extension opening. The tube extension is movable between an attached position and a detached position. At the attached position, the tube extension is secured to the tube by frictional contact between the extension wall and the tube at the distal tube opening. At the detached position the tube extension is physically separate from the tube. The sorbent bed is disposed at an axial distance from the distal tube opening and in the tube or the tube extension. The sorbent bed has a composition configured for solid phase extraction.

9 Claims, 6 Drawing Sheets

(56) References Cited

U.S. PATENT DOCUMENTS

| | | | |
|---|---|---|---|
| 5,415,758 | A | 5/1995 | Comeau |
| 5,427,953 | A | 6/1995 | Yee |
| 5,432,097 | A | 7/1995 | Yourno |
| 5,460,057 | A | 10/1995 | Ostrup |
| 5,496,626 | A | 3/1996 | Hamajima et al. |
| 5,508,200 | A | 4/1996 | Tiffany et al. |
| 5,516,487 | A | 5/1996 | Rosenthal et al. |
| 5,906,796 | A | 5/1999 | Blevins et al. |
| 5,906,947 | A | 5/1999 | Bienhaus |
| 6,048,457 | A | 4/2000 | Kopaciewicz et al. |
| RE36,717 | E * | 5/2000 | Thompson ............ 426/518 |
| 6,176,867 | B1 * | 1/2001 | Wright ............ 606/184 |
| 6,200,474 | B1 | 3/2001 | Kopaciewicz et al. |
| 6,200,533 | B1 | 3/2001 | Blevins et al. |
| 6,416,716 | B1 | 7/2002 | Shukla et al. |
| 6,491,873 | B2 | 12/2002 | Roberts et al. |
| 6,566,145 | B2 * | 5/2003 | Brewer ............ 436/178 |
| 7,595,026 | B2 | 9/2009 | Hudson et al. |
| 7,638,099 | B2 | 12/2009 | Lloyd et al. |
| 2001/0001643 | A1 | 5/2001 | Simpson et al. |
| 2002/0058027 | A1 * | 5/2002 | Nelson et al. ............ 424/94.63 |
| 2002/0110495 | A1 * | 8/2002 | Hunt et al. ............ 422/101 |
| 2002/0164272 | A1 | 11/2002 | Harris |
| 2005/0066751 | A1 | 3/2005 | Harris |
| 2006/0057738 | A1 * | 3/2006 | Hall ............ 436/177 |
| 2006/0246419 | A1 * | 11/2006 | Thornton et al. ............ 435/4 |
| 2008/0277347 | A1 | 11/2008 | Grenz |

OTHER PUBLICATIONS

Communication for EP 11 182 834.9-1553 dated Jun. 13, 2014.

* cited by examiner

APPARATUS FOR PUNCHING AND SOLID PHASE EXTRACTION OF DRIED BIOLOGICAL FLUID SPOT AND RELATED METHODS

FIELD OF THE INVENTION

The present invention relates generally to dried biological fluid spot analysis and the formation and processing of dried biological fluid spot samples in preparation for subsequent analysis.

BACKGROUND OF THE INVENTION

Dried biological fluid spot analysis such as dried blood spot (DBS) analysis is becoming increasingly popular for pharmaceutical companies in clinical trials. Collection sites for clinical trials may sample blood spots (or other types of biological fluid spots) in the field, allow the spots to dry, and then ship the spots at a lower cost than liquid samples due to the non-biohazard status of dried blood spots and the less rigorous requirements for temperature control. Blood spotting is also becoming useful in preclinical work as analytical chemists are required to store samples for Incurred Sample Reanalysis (ISR) studies, and dried blood spots have proven to be an effective way to stabilize the analytes and the matrix. Typically, DBS samples are prepared by applying drops of blood, typically obtained from venipuncture of a human or animal, to an absorbent substrate (e.g., filter paper) of an appropriate composition. The blood saturates the substrate and is air dried for a period of time (e.g., several hours) sufficient to form an array of circular dried blood spots on the substrate. The spot-containing substrate may then be stored in a plastic container and transported as needed without needing to be frozen. The dried blood spots may thereafter be separated from the bulk substrate by punching the dried blood spots to create individual dried blood spot disks. Analytes such as pharmaceutical compounds, genetic materials, etc. (i.e., small molecules or high molecular weight molecules) may then be extracted from dried blood spots by any number of techniques and subjected to analytical testing. Other types of biological fluid samples may be dried and subsequently processed in an analogous manner.

The processing of dried blood spots and other types of biological fluid spots has many problems. For instance, labs typically utilize a single punching device for multiple sample spotting procedures. Even with the use of cleaning and sterilization procedures, the repeated use of the same punching device can cause carryover and cross-contamination. In addition, the conventional punch device is typically constructed of steel so as to be hard or strong enough to punch through conventional spotting substrates. The steel punching device often must be employed with a hammer to achieve effective punching Moreover, steel is generally not considered to be readily disposable as compared to other types of materials such as various plastics. Additionally, procedures such as extraction and collection of analytes and pass-through cleanup have conventionally required the use of instruments separate from the punch device. Typically protein precipitation or solid phase extraction is utilized to transfer the sample to a suitable matrix, remove interferences and concentrate or dilute the sample as necessary. Also, conventional processing of dried biological fluid spots has not been compatible with automated assaying systems.

In view of the foregoing, there is a need for providing apparatus or device configured for performing both punching and extraction/clean-up, and methods for punching and processing dried biological fluid spots utilizing a single apparatus or device capable of being implemented for both punching and processing. Additionally, there is a need for an apparatus or device that is readily disposable and thus readily replaceable after a single use.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, an apparatus for punching and extracting analytes from a dried biological fluid spot includes a tube and a sorbent bed. The tube includes a proximal tube end circumscribing a proximal tube opening, a distal tube end circumscribing a distal tube opening having an inside diameter less than an inside diameter of the proximal tube opening, and a distal section composed of an inert organic polymer having a Rockwell hardness of 89 or greater. The distal section includes a distal tube wall having a tapered inside diameter that reduces in a direction from the proximal tube end to the distal tube end. The distal tube wall includes a first section and a second section adjoining the first section and extending to the distal tube end. The first section has a first section thickness. The second section has a second section thickness tapering from the first section thickness to a thickness of the distal tube end less than the first section thickness, wherein the distal tube end comprises a sharp edge. The sorbent bed is disposed at an axial distance from the distal tube opening, the sorbent bed having a composition configured for solid phase extraction.

In some implementations, the first section thickness ranges from 0.5 to 8 mm.

According to another implementation, an apparatus for punching and extracting analytes from a dried biological fluid spot includes a tube, a tube extension, and a sorbent bed. The tube includes a proximal tube end circumscribing a proximal tube opening, a distal tube end circumscribing a distal tube opening having an inside diameter less than an inside diameter of the proximal tube opening, and a distal section terminating at the distal tube end. The distal section includes a distal tube wall having a tapered inside diameter that reduces in a direction from the proximal tube end to the distal tube end. The tube extension includes a proximal extension end circumscribing a proximal extension opening, a distal extension end circumscribing a distal extension opening, and an extension wall having a tapered inside diameter that reduces from the proximal extension opening to the distal extension opening. The proximal extension opening has an inside diameter greater than an outside diameter of the distal tube end, and the distal extension opening has an inside diameter less than the inside diameter of the distal tube opening. The tube extension is movable between an attached position and a detached position. At the attached position, the tube extension is secured to the tube by frictional contact between the extension wall and the distal tube end, and the distal extension opening fluidly communicates with the distal tube opening. At the detached position the tube extension is physically separate from the tube. The sorbent bed is disposed at an axial distance from the distal tube opening and in the tube or the tube extension. The sorbent bed has a composition configured for solid phase extraction.

In some implementations, the sorbent bed is disposed in the tube. In other implementations, the sorbent bed is disposed in the tube extension and is detachable with the tube extension from the tube.

In some implementations, the thickness of the distal tube wall at the distal tube opening is 0.5 mm or greater. In other implementations, the thickness may range from 0.5 to 8 mm.

In some implementations of any of the apparatus, the tube encloses a volume between the proximal tube end and the distal tube end, and the volume ranges from 100 to 5000 μL.

In some implementations of any of the apparatus, the tube is composed of a polyolefin, polypropylene, polyethylene, polyamide, polyacrylate, or a combination of two of more of the foregoing.

In some implementations of any of the apparatus, the axial distance of the sorbent bed from the distal tube opening ranges from 1 to 5 mm.

In some implementations of any of the apparatus, the distal tube opening has a diameter ranging from 1 to 6 mm.

According to another implementation, a method is provided for acquiring a biological fluid sample from a substrate that includes one or more dried biological fluid spots. A dried biological fluid sample unit is formed. The sample unit includes a portion of the substrate and a selected dried biological fluid spot carried by the portion. The sample unit is formed by operating a tube composed of an inert polymer and including a sharp distal tube end circumscribing a distal tube opening. The tube is operated to punch through the substrate at the portion, wherein the dried biological fluid sample unit is separated from the substrate, passes through the distal tube opening and is positioned in the tube. Analytes are eluted from the dried biological fluid sample unit and retained on a sorbent bed by flowing a first elution solvent through the tube and through the sorbent bed. An analyte-inclusive liquid sample matrix is formed by flowing a second elution solvent through the sorbent bed to desorb the analytes from the sorbent bed.

According to another implementation, a method is provided for acquiring a biological fluid sample from a substrate that includes one or more dried biological fluid spots. A dried biological fluid sample unit is formed. The sample unit includes a portion of the substrate and a selected dried biological fluid spot carried by the portion. The sample unit is formed by operating a tube to punch through the substrate at the portion, separating the sample unit from the substrate, passing the sample unit through a distal opening of the tube, and positioning the sample unit in the tube. A tube extension is attached to a distal tube end of the tube circumscribing the distal tube opening. The tube extension includes a proximal extension opening, a distal extension opening of lesser inside diameter than an inside diameter of the distal tube opening, and an extension wall having a tapered inside diameter that reduces from the proximal extension opening to the distal extension opening. The tube extension is attached by inserting the distal tube end through the proximal extension opening and urging the distal tube end into frictional contact with the extension wall to form a liquid seal between the distal tube end and the extension wall. Analytes are eluted from the dried biological fluid sample unit and retained on a sorbent bed disposed in the tube or the tube extension, by flowing a first elution solvent through the tube, the tube extension and the sorbent bed. An analyte-inclusive liquid sample matrix is formed by flowing a second elution solvent through the sorbent bed to desorb the analytes from the sorbent bed.

According to another implementation, a method is provided for acquiring a biological fluid sample from a substrate that includes one or more dried biological fluid spots. A dried biological fluid sample unit is formed. The sample unit includes a portion of the substrate and a selected dried biological fluid spot carried by the portion. The sample unit is formed by operating a tube composed of an inert polymer and including a sharp distal tube end circumscribing a distal tube opening The tube is operated to punch through the substrate at the portion, wherein the dried biological fluid sample unit is separated from the substrate, passes through the distal tube opening and is positioned in the tube. An analyte-inclusive liquid sample matrix is formed by flowing an elution solvent through the sorbent bed, wherein analytes are eluted from the dried biological fluid sample unit and pass through the sorbent bed while non-analytical material is retained on the sorbent bed.

According to another implementation, a method is provided for acquiring a biological fluid sample from a substrate that includes one or more dried biological fluid spots. A dried biological fluid sample unit is formed. The sample unit includes a portion of the substrate and a selected dried biological fluid spot carried by the portion. The sample unit is formed by operating a tube to punch through the substrate at the portion, separating the sample unit from the substrate, passing the sample unit through a distal opening of the tube, and positioning the sample unit in the tube. A tube extension is attached to a distal tube end of the tube circumscribing the distal tube opening. The tube extension includes a proximal extension opening, a distal extension opening of lesser inside diameter than an inside diameter of the distal tube opening, and an extension wall having a tapered inside diameter that reduces from the proximal extension opening to the distal extension opening. The tube extension is attached by inserting the distal tube end through the proximal extension opening and urging the distal tube end into frictional contact with the extension wall to form a liquid seal between the distal tube end and the extension wall. An analyte-inclusive liquid sample matrix is formed by flowing an elution solvent through the sorbent bed. Analytes are eluted from the dried biological fluid sample unit and pass through the sorbent bed, while non-analytical material is retained on the sorbent bed.

According to any of the methods, the method may further include subjecting the analyte-inclusive liquid sample matrix to an analytical procedure, such as protein precipitation, fraction collection, centrifugation, spectrophotometry, nuclear magnetic resonance spectrometry, solid phase extraction, chromatography, and/or genetic testing.

According to any of the methods, the dried biological fluid spot may be a dried blood spot and the liquid sample matrix may be a blood component-inclusive matrix.

According to another implementation, a kit is provided for a dried biological fluid spot punch device. The kit includes one or more tubes and one or more sorbent beds. The kit may also include one or more tube extensions and/or one or more frits.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In the context of the present disclosure, the term "fluid" refers generally to liquid-phase materials and gas-phase materials, unless a liquid-phase material or a gas-phase material is specifically indicated. The terms "liquid-phase" and "liquid," and "gas-phase" and "gas," are used interchangeably. A liquid-phase material or liquid may be any liquid, such as a solution, suspension, slurry, multi-phase mixture or the like, and may include gaseous components (e.g., bubbles) and/or solid components (e.g., particles). A gas-phase material or gas may be any gas or vapor, and may include liquid components (e.g., droplets) and/or solid components (e.g., particles). A "dried fluid sample" or a "dried fluid spot" refers generally to a material that was initially provided in the liquid phase and was thereafter dried, such as by air drying.

In the context of the present disclosure, the term "analyte" refers generally to any sample molecule of interest—that is, a molecule on which an analysis is desired such as, for example, a chromatographic analysis.

In the context of the present disclosure, the term "sample matrix" refers to any combination of analytes and non-analytes. The combination of analytes and non-analytes may exist in a liquid phase and/or a gas phase. "Non-analytes" in this context refer to components of the sample matrix for which analysis is not of interest because such components do not have analytical value and/or impair the analysis of the desired analytes. Examples of non-analytes may include water, oils, or other media in which the desired analytes may be found, molecules not of interest, as well as solvents, buffers, reagents, and various solid particles such as excipients, precipitates, fillers, and impurities.

In the context of the present disclosure, the term "diameter" refers in a general sense to the characteristic dimension of any shape and therefore does not necessarily imply a circular shape. As examples, the characteristic dimension of a tube of circular cross-section may be considered a diameter, the characteristic dimension of a tube of elliptical cross-section may be considered a major axis, and the characteristic dimension of a tube of polygonal cross-section may be considered the length (width) of a side or the distance between two inside corners. For convenience, the term "diameter" encompasses all such types of characteristic dimensions.

Figure 1:
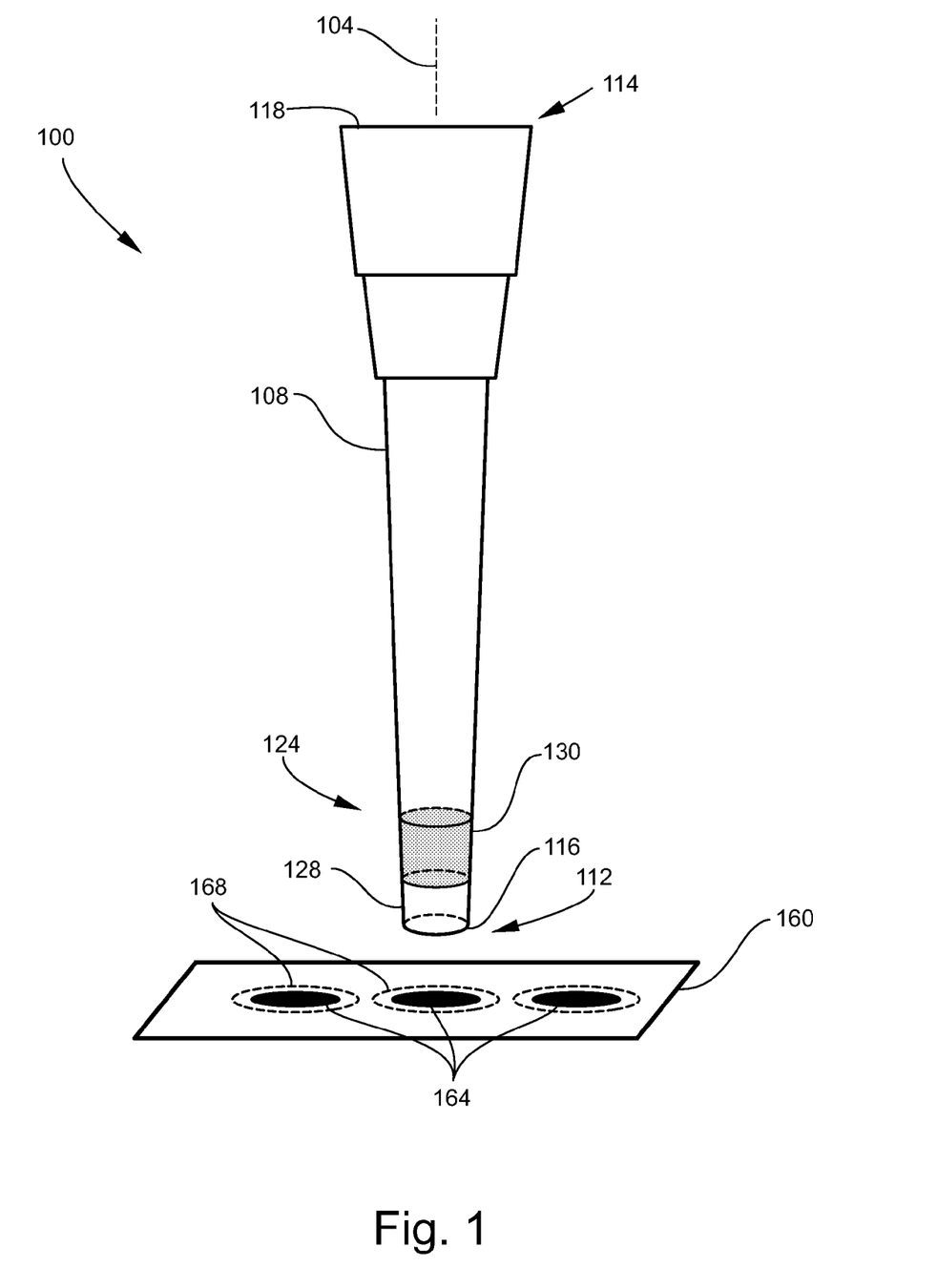
FIG. 1 is an elevation view of an example of a tube according to an implementation of the present teachings, and also illustrates an example of a substrate containing one or more spots of dried biological fluid.

FIG. 1 is an elevation view of an example of a tube (or pipette, etc.) 100 according to an implementation of the present teachings. The tube 100 is generally situated along a longitudinal axis 104. In FIG. 1 and in typical implementations, the tube 100 has a generally straight orientation along the longitudinal axis 104, while in other implementations the tube 100 may include one or more curved or angled sections. The tube 100 generally includes a hollow body 108 coaxial with the longitudinal axis 104. The hollow body 108 may include a single tube wall or two or more adjoined walls. The hollow body 108 defines an internal cross-sectional area which, from the perspective of FIG. 1, is orthogonal to the longitudinal axis 104. The cross-sectional area may be circular as in the illustrated example, or alternatively may be elliptical or polygonal. The tube 100 (i.e., the hollow body 108) terminates at a distal tube end 112 and an axially opposite proximal tube end 114. The distal tube end 112 circumscribes a distal tube opening 116, and the proximal tube end 114 circumscribes a proximal tube opening 118. In typical implementations, the inside diameter of the distal tube opening 116 is less than the inside diameter of the proximal tube opening 118. The tube 100 further includes a distal section (or pipette tip) 124 generally defined by a portion of the hollow body 108 that extends to (terminates at) the distal tube opening 116. The distal section 124 includes a tapered distal tube wall 128 such that the inside diameter of the distal section 124 tapers in the axial direction generally toward the distal tube end 112, whereby the distal tube opening 116 is the minimum inside diameter of the distal section 124. Both the inside surface and the outside surface of the wall of the distal section 124 may be tapered (relative to the longitudinal axis 104), as illustrated in FIG. 1. The tapered geometry may or may not continue over the remaining length of the tube 100. The upper portion of the tube 100 (proximate to and including the proximal tube end 114) may be configured as desired for coupling to any suitable means for flowing liquid through the tube 100 in either or both axial directions (e.g., vacuum manifold, positive-pressure pump, aspiration or fill tubing, etc.).

The tube 100 encloses a volume extending along the longitudinal axis 104 from the proximal tube opening 118 to the distal tube opening 116. In typical implementations, the volume ranges from 100 µL to 5,000 µL (5 mL), while in other implementations the volume may be less than 100 µL or greater than 5 mL. In one non-limiting example, the volume is 300 µL. In typical implementations, the inside diameter of the distal tube opening 116 ranges from 1 to 6 mm. In some implementations, the inside diameter of the distal tube opening 116 ranges from 3 to 4 mm. In some implementations the tube 100 is intended for insertion into the well of a multi-well plate (or other type of container), a centrifuge tube, or other receptacle. In such implementations, the outside diameter of the tube 100 (at least that portion of the tube 100 intended for insertion into the receptacle) should be slightly less than the inside diameter of the receptacle into which the tube 100 is to be inserted. For instance, in typical multi-well plates, the inside diameter of each well ranges from 3 mm to 8 mm.

The tube 100 may have any suitable inert (i.e., non-reactive and non-binding) composition, particularly an organic polymer. In the present context, the term "polymer" encompasses homopolymers, copolymers, and polymer blends. Examples of suitable polymers include, but are not limited to, polypropylene, polyethylene, other polyolefins, polyamide, polyacrylate, a combination of two of more of the foregoing, and more generally any chemically inert plastic formable into a tube or fit such as by injection molding or other suitable fabrication technique. Generally, such polymers may be considered to be inexpensive and readily disposable as compared to steel and other metals. In some implementations, the tube 100 has an inert polymer composition such as just specified, and further the polymer is one which is hard enough to enable a user to effectively punch through a substrate 160 of various compositions and thicknesses (examples of which are noted below) without failure of the tube 100. In some implementations, the tube 100 is an inert polymer having (exhibiting) a Rockwell hardness of at least 89 (ranging from 89 or greater) as measured by the Rockwell hardness test R, American Society for Testing and Materials (ASTM) method D785-08 (2008). In one specific yet non-limiting example, the tube 100 is composed of polypropylene of a formulation having a Rockwell hardness of 89.

In the present implementation, the tube 100 further includes a sorbent bed (or plug or packing of sorbent material) 130 positioned at an axial distance from the distal tube opening 116. The sorbent bed 130 may have any configuration suitable for retaining analytes (or non-analytes such as in a pass-through clean-up configuration) according to mechanisms generally associated with solid phase extraction (SPE) or chromatography. In some implementations the sorbent bed 130 is a mass of particles while in other implementations is a mass of fibers, as appreciated by persons skilled in the art. Examples of the composition of the sorbent bed 130 include, but are not limited to, various organic polymers (homopolymers, copolymers, or polymer blends), glass fiber cellulose, silica, ion exchange modified silica, C8, C18, amide, amino, diol, and combinations of two or more of the foregoing. In some implementations, the sorbent bed 130 is composed of a glass fiber matrix that includes (e.g., is embedded with) a bonded phase such as a metal oxide or metalloid oxide. The metal oxide or metalloid oxide is typically one that is capable of reacting with silanes, such as alkoxysilanes, aminosilanes, hydroxysilanes or halosilanes. Examples of suitable metal oxides and metalloid oxides include, but are not limited to, silica, alumina, zeolite, mullite, zirconia, vanadia or titania, and mixtures or composites thereof. The metal oxide or metalloid oxide may functionalized (chemically treated) by a functional moiety. Examples of functional moieties include, but are not limited to, hydrocarbyl (e.g., $C_{2-30}$ alkyl, alkenyl, alkynyl), —NHC(O)— (amido), —C(O)NH— (carbamyl), —OC(O)NH— (carbamato), —NHC(O)O— (urethane), —NHC(O)NH— (carbamido or urea), —NCO (isocyanato), —CHOHCHOH— (diol), $CH_2OCHCH_2O$— (glycidoxy), —$(CH_2CH_2O)_n$— (ethoxy), —$(CH_2CH_2CH_2O)_n$— (propoxy), —C(O)— (carbonyl), —C(O)O— (carboxy), $CH_3C(O)CH_2$—(acetonyl), —S— (thio), —SS— (dithio), —CHOH— (hydroxy), —O— (ether), —SO— (sulfinyl), —$SO_2$—(sulfonyl), —$SO_3$— (sulfonic acid), —$OSO_3$— (sulfate), —$SO_2NH$—, —$SO_2NMe$— (sulfonamido), —NH—, —NMe-, —$NMe_2^+$-, —$N[(CH_2)_n]_2^+$— (amino), —CN (nitrilo), —NC (isonitrilo), —CHOCH— (epoxy), —NHC(NH)NH— (guanidino), —$NO_2$ (nitro), —NO (nitroso), and —$OPO_3$— (phosphate), where Me is methylene or methyl, and where n is an integer up to 30, typically less than 10.

The sorbent bed 130 may be installed in the tube 100 by any suitable technique, such as by fabricating a bulk quantity of the sorbent material, cutting a desired quantity of the sorbent material, inserting the sorbent material into the tube 100 via the proximal tube opening 118, and utilizing a needle or other tool to position the sorbent material at a desired axial distance from the distal tube opening 166 to form a sorbent bed 130 that spans the cross-sectional flow area of the tube 100. The sorbent bed 130 may be compressed as needed to attain a desired density and average size of interstices. The sorbent bed 130 may be fixed in position in the distal section 124, i.e., at an axial elevation near the distal tube opening 166 where the sorbent bed contacts the tapered tube wall 128. In some implementations, the sorbent bed 130 has a mass ranging from 1 to 20 mg, and in other implementations has a mass ranging from 1 to 10 mg. In typical implementations, sorbent bed 130 is held in place at an axial distance from the distal tube opening 116 ranging from 1 to 5 mm.

Figure 2A:
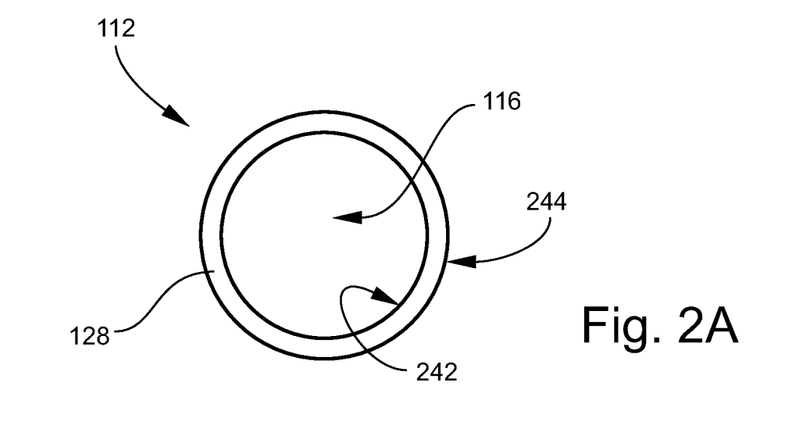
FIG. 2A is a plan view of a distal tube end of the tube illustrated in FIG. 1.

The tube 100 is utilized as a dried fluid spot punch device as well as an SPE device. Hence, the distal tube end 112 is configured for punching through substrates having compositions and thicknesses contemplated for the tube 100. The distal tube end 112 may be characterized as being "sharp" enough to punch through substrates of interest. FIG. 2A is a plan view of the distal tube end 112. One way to describe the sharpness of the distal tube end 112 is in terms of the thickness of the tube 100 (i.e., the tube wall 128) at the distal tube end 112, i.e., the thickness between an inner surface 242 and an outer surface 244 of the tube 100 at the distal tube end 112. In some implementations, the thickness of the tube 100 at the distal tube end 112 ranges from 0.5 mm or greater, such as 0.5 mm to 8 mm. In other implementations, the thickness of the tube 100 at the distal tube end 112 may range from 2 mm to 8 mm. In some implementations, an example of which is described below in conjunction with FIG. 2B, the thickness of the tube 100 tapers down to a sharp edge at the distal tube end 112, such that the thickness of the sharp edge is less than 0.5 mm. In some implementations, the outer surface 244 (and thus the outside diameter) of the tube 100 may taper outwardly from the distal tube end 112 in the direction of the longitudinal axis 104 (FIG. 1), in a manner analogous to the tip of a hollow needle.

Figure 2B:
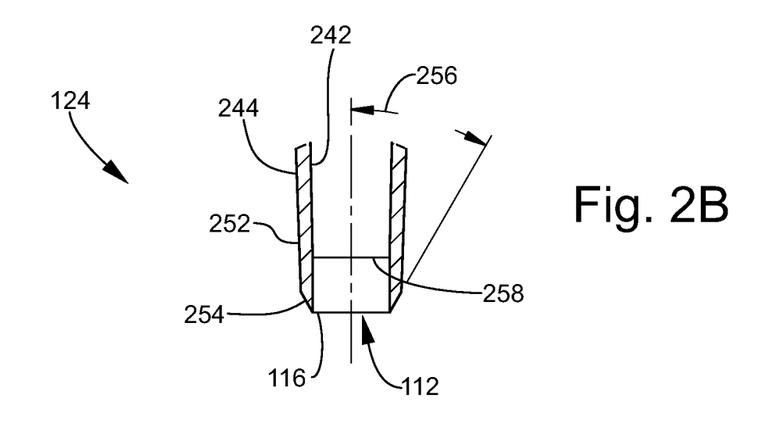
FIG. 2B is a cross-sectional elevation view of an example of a distal section of the tube illustrated in FIG. 1.

FIG. 2B is a cross-sectional elevation view of an example of the distal section 124 of the tube 100 according to some implementations. In this example, the distal section 124 includes a first section 252 and a second section 254 adjoining the first section 252. The second section 254 axially extends from the first section 252 to the distal tube end 112. The first section 252 has a thickness (between the inner surface 242 and the outer surface 244 of the tube 100) of at least 0.5 mm (i.e., the first section thickness is 0.5 mm or greater) or other range as described above in conjunction with FIG. 2A, at least at the location where the first section 252 adjoins the second section 254. The second section 254 is configured such that the distal section 124 of the tube 100 terminates at a sharp edge (i.e., the distal tube end 112 is sharp), which facilitates the use of the tube 100 as a punch tool for a spotting substrate 160. In the present implementation, this sharpness is implemented as follows. The second section 254 has a thickness that tapers down to the distal-most edge of the distal tube end 112. Hence, the thickness of the second section 254 at the distal tube end 112 is less than the thickness of the first section 252, i.e. is less than 0.5 mm. In the example illustrated in FIG. 2B, the tapering of the second section 254 is implemented by the outer surface 244 of the portion of the distal section 124 comprising the second section 254 being oriented at a greater angle relative to the axis of the distal section 124 than the remaining (upper) portion of the distal section 124. In some implementations, the second section 254 has an angle ranging from 20° to 50° relative to the axis. In another implementation, the angle of the second section 254 is 30° relative to the axis.

As also illustrated in FIG. 2B, in some implementations, the distal section 124 includes an inner shoulder (or rib) 258 formed around the inner surface 242 and protruding toward the axis. The inner shoulder 258 may be a complete annular shoulder that traverses the circumference of the inner surface 242, or the inner shoulder 258 may include one or more structures circumferentially spaced apart from each other about the axis. The inner shoulder 258 may protrude from the inner surface 242 by a small amount, for example 0.25 mm. The inner shoulder 258 may be utilized to support the sorbent bed 130. Thus, the inner shoulder 258 may be located at an axial distance ranging from 1 mm to 5 mm from the distal tube end 112. In one example, the inner shoulder 258 is located at about 2.5 mm from the distal tube end 112.

Figure 3:
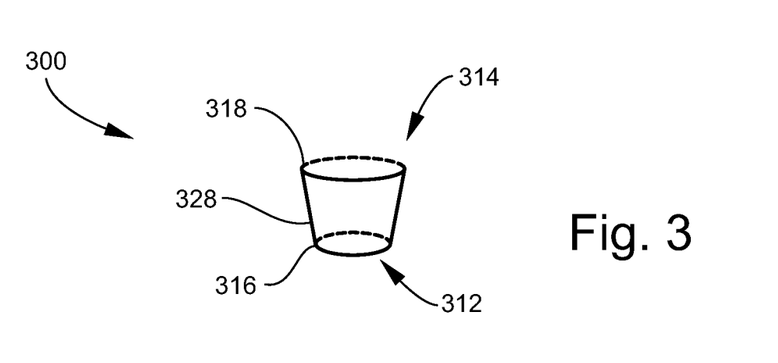
FIG. 3 is an elevation view of an example of a tube extension that may be utilized in conjunction with the tube illustrated in FIG. 1.

FIG. 3 is an elevation view of an example of a tube extension 300 that may be utilized in conjunction with the tube 100 in some implementations. The tube extension 300 includes a distal extension end 312 circumscribing a distal extension opening 316, a proximal extension end 314 circumscribing a proximal extension opening 318, and an extension wall 328 that tapers from the proximal tube opening 318 to the distal tube opening 312. The tube extension 300 may, for example, have a frusto-conical shape. The tube extension 300 is configured to be securely attached to the tube 100 at the distal tube opening 116, as described in more detail below. The inside diameter of the tube extension 300 at the proximal extension opening 318 is greater than the outside diameter of the tube 100 at the distal tube opening 116, and the inside diameter of the tube extension 300 at the distal extension opening 316 is less than the inside diameter of the distal tube opening 116. The composition of the tube extension 300 may be the same as or different from the composition of the tube 100.

FIG. 1 also illustrates an example of utilizing the tube 100 as a punch device. The tube 100 is held over a substrate (or card, etc.) 160 in which one or more spots 164 of dried biological fluid have been formed. Examples of biological fluids that may be formed into dried spots 164 using the substrate 160 include, but are not limited to, blood-based samples such as whole blood, plasma or serum. In these cases, the spot-containing substrate 160 is often termed a dried blood spotting card. It will be appreciated, however, that biological fluids formable into dried spots 164 are not limited to blood-based samples. The substrate 160 may be composed of any composition suitable for use as a spotting card, non-limiting examples of which include various types of cellulosic filter papers, glass fiber/cellulose composites, cellulose-free glass fiber paper, polyamides (e.g., nylon), propylene, nitrocellulose, polyethersulfone, etc. In some implementations, the substrate material has a composition and thickness suitable for enabling a tube 100 of an inert polymer composition and hardness (as given by examples above) to be manipulated by a user to effectively punch through the substrate 160 to create a dried biological sample unit 464 (FIG. 4, described below) suitable for further processing. That is, in some implementations the substrate material is of the type that does not require the use of a punch device of steel or other metallic construction. This type of substrate material may be considered as being a "soft" material relative to the "hard" polymer of the tube 100, and thus will typically have a Rockwell hardness value of less than 89 (and in advantageous implementations significantly less than 89). Examples of soft substrate materials suitable for sample spotting include, but are not limited to, cellulose-free glass fiber paper and other materials of similar hardness and therefore capable of being punched by a polymer tube 100 of Rockwell hardness of 89 or greater. The thickness of the soft substrate 160 may range from 0.010 inch to 0.050 inch (0.25 mm to 1.3 mm). Preferably, the substrate material is able to uniformly absorb a biological fluid sample to form a homogeneous circular spot 164. Indicia 168 such as dashed circles may be provided on the substrate 160 for assisting in placement of multiple biological fluid samples when it is desired to form an array of dried biological fluid spots 164. The indicia 168 may be printed matter; perforations or scoring are not required in the use of the tube 100.

Figure 4:
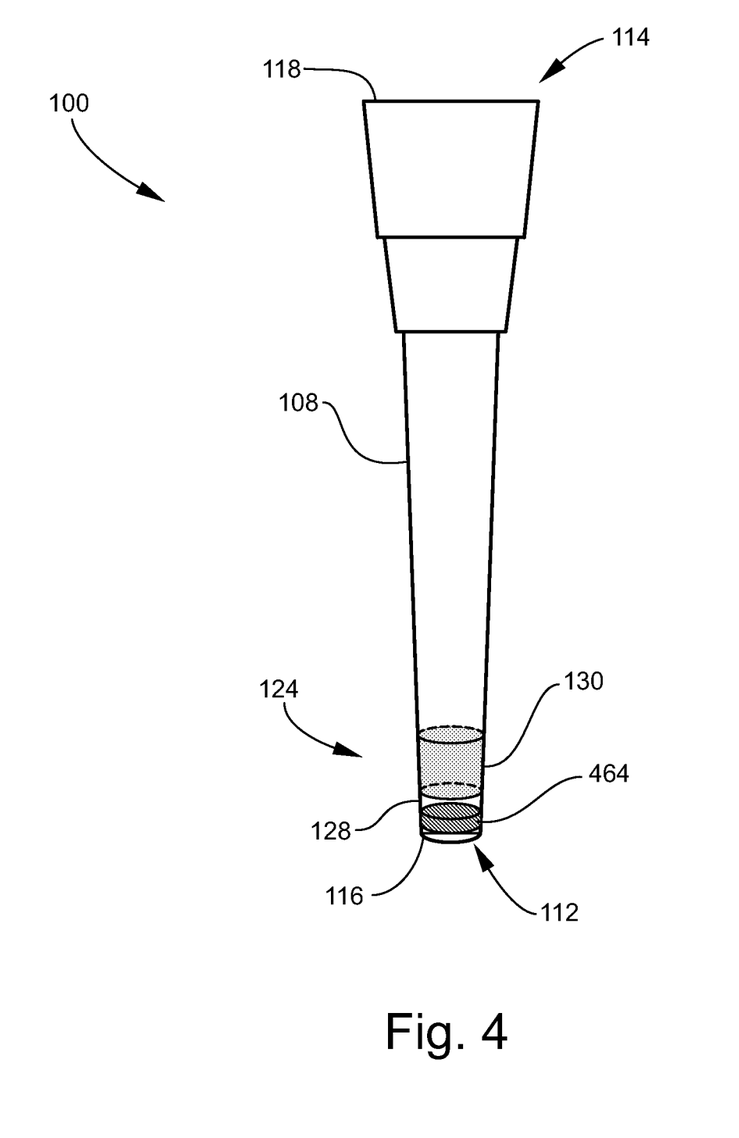
FIG. 4 is an elevation view of the tube illustrated in FIG. 1 after a dried biological fluid sample unit has been punched from the substrate and captured in a distal section of the tube.

To form a dried biological fluid sample unit 464 (FIG. 4), the substrate 160 is supported by any suitable means, the tube 100 (and particularly the distal tube end 112) is aligned with a selected dried biological fluid spot 164, and the tube 100 is thrust downward into the selected dried biological fluid spot 164 and through the portion of the substrate 160 containing the selected dried biological fluid spot 164. As the distal tube end 112 is pushed into the material of the substrate 160 and begins to cut the material, the as-forming sample unit 464 may be bent upwards and into the distal section 124 of the tube 100. In this manner, a sample unit 464 of greater diameter (or other characteristic dimension) than the distal tube opening 116 eventually separates from the substrate 160 and fully passes through the distal tube opening 116 and into the distal section 124. The shape of the sample unit 464 will depend on the shape of the distal tube end 112. In a typical example in which the distal tube end 112 is circular, the sample unit 464 is shaped as a disk. FIG. 4 is an elevation view illustrating the tube 100 after the sample unit 464 has been formed and captured in the distal section 124. After fully passing through the distal tube opening 116, the sample unit 464 may spread or spring outward and become lodged against the inner surface of the distal section 124 by frictional contact, at an axial location between the sorbent bed 130 and the distal tube opening 116. The sample unit 464 may be fixed in position in this manner at an axial distance below the sorbent bed 130, or may abut the underside of the sorbent bed 130. At this time, the tube 100 with the captured sample unit 464 may be transported to an analytical device or any other desired destination. In some implementations, at this time the tube extension 300 (FIG. 3) may be attached to the tube 100 as described below.

Figure 5:
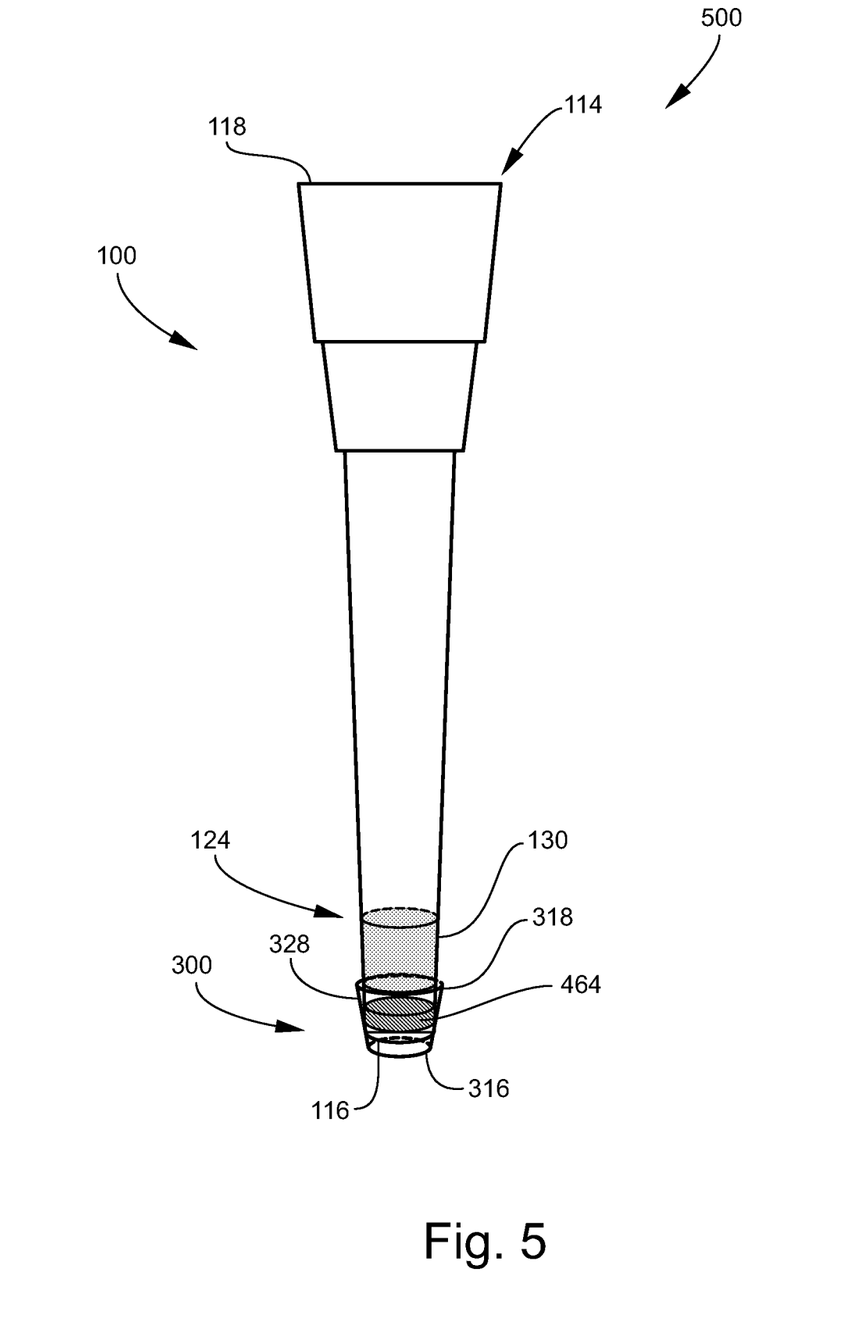
FIG. 5 is an elevation view of an example of an apparatus for punching and extracting analytes from a dried biological fluid spot, including the tube illustrated in FIG. 1 and the tube extension illustrated in FIG. 3 attached to the tube.

FIG. 5 is an elevation view of an example of an apparatus (or device) 500 for punching and extracting analytes from a dried biological fluid spot. The apparatus 500 may also be referred to as a punch/SPE apparatus or device. The apparatus 500 includes the tube 100 and the tube extension 300 attached to tube 100. To effect attachment, the tube extension 300 may be initially supported in a fixed position by a rack or other support structure (not shown) or held by hand. The distal tube end 112 (FIG. 4) is inserted through the proximal extension opening 318 and the tube 100 is pushed downward until the distal tube end 112 is urged into frictional contact with the tapered inside surface of the tube extension 300, thereby securing the tube 100 to the tube extension 300. In this assembled form, the tube 100 forms a liquid-tight seal with the tube extension 300 and the distal extension opening 316 is in fluid communication with the distal tube opening 116. As the diameter of the distal extension opening 316 is less than the diameter of the distal tube opening 116, the tube extension 300 may assist in retaining the captured sample unit 464 in a position proximate to the sorbent bed 130 in case the sample unit 464 becomes dislodged or is not large enough to be held in frictional contact with the inside surface of the distal section 124 of the tube 100. In particular, the tube extension 300 enables solvents or other liquids to be flowed through the tube 100 in the direction of the distal tube opening 116 without the risk of losing the sample unit 464. Liquid may also be flowed in the reverse direction, i.e. toward the proximal tube opening 118, without loss of the sample unit 464 due to the presence of the sorbent bed 130. The direction of liquid flow through the apparatus 500 (i.e., both the tube 100 and the tube extension 300, assembled together) will depend on the various method developments for which utilization of the apparatus 500 is contemplated. At this time, the assembled apparatus 500 with the captured sample unit 464 may be transported to an analytical device or any other desired destination.

The apparatus 500 may generally be utilized in any method for acquiring a biological fluid sample from a substrate 160 (FIG. 1) containing one or more dried biological fluid spots 464. According to one implementation, a dried biological fluid sample unit 464 is formed and captured by the tube 100 and the tube extension 300 is then attached in the manner described above. A first elution solvent (or combination or solvents, with or without buffers or other additives, as needed) is then flowed through the apparatus 500 from the distal extension opening 316, through the distal tube opening 116, around and/or through the sample unit 464, through the sorbent bed 130, and through the proximal tube opening 118. The flow of the first elution solvent may be assisted by gravity (with the tube 100 inverted), centrifugation, vacuum applied at the proximal tube opening 118 and/or positive pressure (e.g., via a syringe) applied at the distal extension opening 316. While the first elution solvent is flowing the sample unit 464 remains captured between the sorbent bed 130 and either the distal tube opening 116 or the distal extension opening 316. The flowing solvent causes analytes to be eluted from the sample unit 464, carried to the sorbent bed 130, and retained on (i.e., on and/or in) the sorbent bed 130. After elution from the sample unit 464 is complete, the tube extension 300 may be detached from the tube 100 and the sample unit 464 may be removed from the tube 100 by any suitable technique such as, for example, by flowing a wash solvent through the tube 100 in the direction of the distal tube opening 116 with enough force to eject the sample unit 464 out from the distal tube opening 116. The tube 100 is then transported to a suitable receptacle (not shown) for collecting an analyte-inclusive liquid sample matrix. For example, the tube 100 may be positioned over or in a selected well of a standard-format multi-well plate, or positioned over or in a single-well plate or equivalent structure (e.g., a sample vial, cuvette, container, etc.), or installed in a centrifuge, etc. The receptacle may be configured for use in conjunction with an automated liquid handling apparatus. The analytes are then desorbed from the sorbent bed 130 by flowing a second elution solvent through the tube 100 and the sorbent bed 130 in the direction of either the proximal tube opening 118 or the distal tube opening 116, thereby forming an analyte-inclusive liquid sample matrix suitable for subsequent analysis.

The types of solvents utilized for elution generally depend on the type of analytes to be eluted from the sample unit 464 and the types of analytes to be desorbed from the sorbent bed 130. Examples of elution solvents include, but are not limited to, methanol, acetonitrile, ethanol, ethyl acetate, methyl tert-butyl ether, dichloromethane, chloroform, and water.

In another implementation of a method for acquiring a biological fluid sample, prior to punching the sample unit 464 the sorbent bed 130 may be conditioned to activate its ligands by flowing a suitable conditioning solvent (e.g., methanol, acetonitrile, etc.) through the tube 100. The conditioning step may include an equilibration sub-step that follows the activation sub-step solvent to adjust pH or control (promote or suppress) ionization, such as flowing water and a pH buffer such as formic acid. The sample unit 464 is then punched and the tube extension 300 attached as described above. A first elution solvent may then be aspirated and dispensed several (e.g., 3-10) times in a clean centrifuge tube to transfer the analytes from the sample unit 464 to the sorbent bed 130. A wash solvent (e.g., water, methanol, or both, with or without a buffer) is then flowed through the tube 100 to elute interferences and impurities without eluting the analytes. At this time, the tube extension 300 may be removed so that the wash solvent is utilized to remove the sample unit 464 as described above. The analytes are then eluted from the sorbent bed 130 by aspirating and dispensing a second elution solvent as described above.

As regards the various methods described herein, it will be understood that any step involving the flow of a solvent or other fluid may be repeated one or more times. In other words, any given step of flowing a fluid may encompass one or more passes through the tube 100 and/or the tube extension 300 as appropriate.

It will be appreciated that the apparatus 500 may generally be utilized in any SPE or chromatographic procedure. For example, the material of the sorbent bed 130 may be configured for retaining certain analytes eluted from the sample unit 464. Analytes retained by the sorbent bed 130 may subsequently be collected by, for example, solvent-based desorption as described above. Alternatively, the sorbent bed 130 may be configured for retaining certain non-analytical material in pass-through clean-up procedures as appreciated by persons skilled in the art. That is, the analytes eluted from the sample unit 464 pass through the sorbent bed 130 unretained while the non-analytical material is retained, thus forming an analyte-inclusive liquid sample matrix via a single elution step. The analytes may then be concentrated or enriched by any suitable technique. The non-analytical material may be any chemical or biological species not of interest to the user, and generally depends on the type of biological fluid sample and/or the analysis to be performed. Examples of non-analytical material may thus include components considered to be interferences, ion suppressing components, salts, surfactants, lipids, proteins, etc. In either case, the sorbent bed 130 may be utilized to improve the sensitivity of subsequent analytical procedures, and more generally may be utilized in the development of a diverse variety of methods.

After creating the analyte-inclusive liquid sample matrix, the analyte-inclusive liquid sample matrix may be processed in any desired manner for separating, concentrating, purifying, and/or analyzing the analytes (i.e., subsequent analytical techniques). Examples of subsequent analytical techniques include, but are not limited to, protein precipitation, fraction collection, centrifugation, spectrophotometry, nuclear magnetic resonance (NMR) spectrometry, various types of SPE (e.g., normal-phase, reversed-phase, ion-exchange, etc.), and various types of chromatography (e.g., preparative chromatography, liquid chromatography (LC), gas chromatography (GC), etc.) as well as hyphenated techniques entailing mass spectrometry (LC/MS$^n$, GC/MS$^n$, etc.). Other subsequent analytical techniques include the testing or processing of genetic material (i.e., "genetic testing") such as ribonucleic acid (RNA) or deoxyribonucleic acid (DNA). Examples of genetic testing include, but are not limited to, polymerase chain reaction (PCR), reverse transcriptase PCR (RT-PCR), ligase chain reaction (LCR), hybridization, genomic sequencing, labeling, assaying, etc. The liquid sample matrix may be collected in a multi-well plate or other receptacle that is then placed in a liquid handling robot for automated subsequent analysis, as appreciated by persons skilled in the art.

Alternatively, the liquid sample matrix may be aspirated from the tube 100 and injected directly into an analytical instrument (e.g., LC, GC, LC/MS$^n$, GC/MS$^n$, etc.). The tube 100 of the apparatus 500, or both the tube 100 and the tube extension 300, may be discarded after use.

It will be understood that the tube extension 300 is optional in some implementations—that is, the tube 100 may be utilized as a punch device and a sample extraction device without the use of the tube extension 300. In such implementations, the apparatus 500 may include only the tube 100 and the sorbent bed 130. An example of a method not employing the tube extension 300 is as follows. A dried biological fluid sample unit 464 is formed as described above. The tube 100 utilized in this example is composed of an inert polymer and includes a sharp distal tube end 112 circumscribing a distal tube opening 116, as described above. To form the sample unit 464, the tube 100 is operated to punch through the portion of the substrate 160 where the target sample spot 164 (FIG. 1) is located, such that the dried biological fluid sample unit 464 containing the sample spot 164 is separated from the substrate 160, passes through the distal tube opening 116 and becomes positioned in the tube 100. Analytes are eluted from the sample unit 464 and retained on a sorbent bed 130 by flowing a first elution solvent through the tube 100 and through the sorbent bed 130. At this stage, the sample unit 464 may be removed by any means, such as by dropping the sample unit 464 out from the tube 100 under the influence of gravity, by employing any suitable tool to grasp the sample unit 464 and withdraw it from the tube 100, or by forcing the sample unit 464 out from the tube 100 under the influence of the flow of the first elution solvent. An analyte-inclusive liquid sample matrix is formed by flowing a second elution solvent through the sorbent bed 130 to desorb the analytes from the sorbent bed 130.

In another example, in which the tube 100 is utilized for sample clean-up and without the use of the tube extension 300, a dried biological fluid sample unit 464 is formed using a sharp-edged (or sharp-tipped) tube 100 as described above. An analyte-inclusive liquid sample matrix is formed by flowing an elution solvent through the sorbent bed 130, wherein analytes are eluted from the sample unit 464 and pass through the sorbent bed 130 while non-analytical material is retained on the sorbent bed 130.

Figure 6:
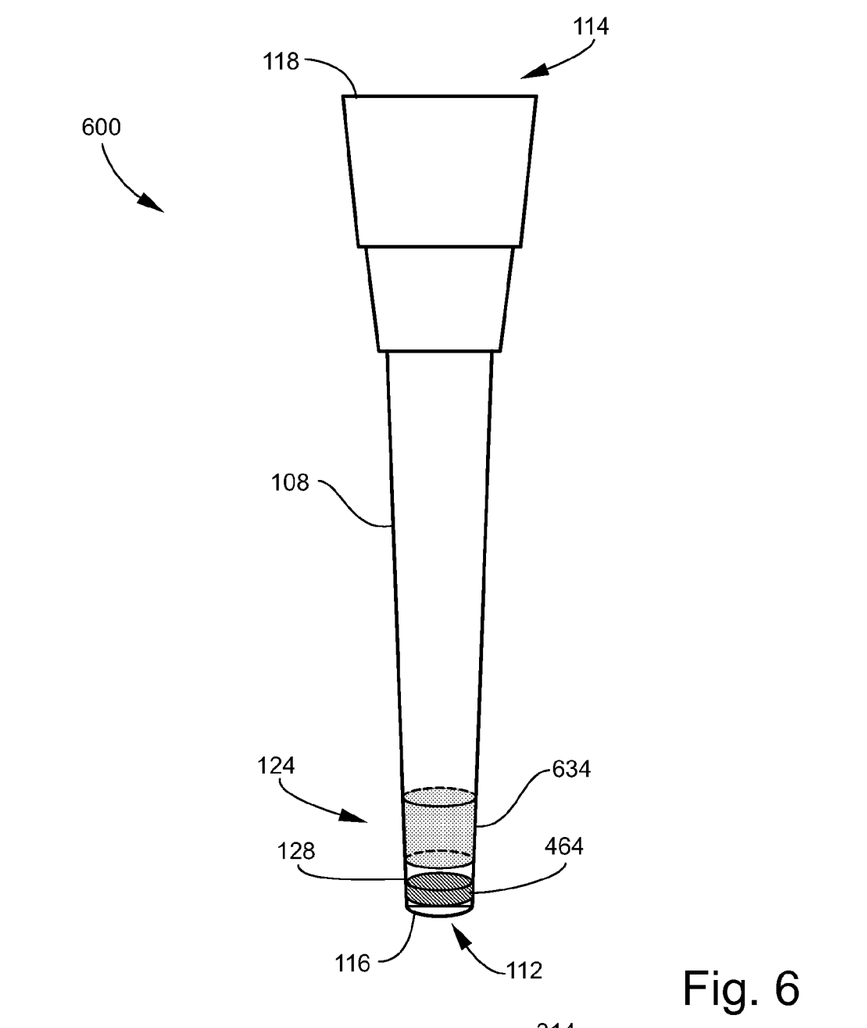
FIG. 6 is an elevation view of another example of a tube according to another implementation of the present teachings.

FIG. 6 is an elevation view of another example of a tube 600. The tube 600 may generally be configured similar to the tube 100 described above and illustrated in FIG. 1. In the tube 600 of the present implementation, however, a frit 634 is installed in place of the sorbent bed 130. The frit 634 is fixed in position in the distal section 124 of the tube 600 so as to span the cross-sectional area of the distal section 124. In the illustrated example, the frit 634 is fixed in position via frictional contact (or press-fit) with the tapered inside surface of the distal section 124. Hence, one way of installing the fit 634 is to load the frit 634 into the tube 600 at the proximal tube opening 118, and then utilize any suitable tool to urge the frit 634 into frictional contact with the distal section 124 in a transverse orientation relative to the longitudinal axis. In typical implementations, the frit 634 is held in place at an axial distance from the distal tube opening 116 ranging from 1 to 5 mm. The frit 634 prevents a punched sample unit 464 from moving toward the proximal tube end 114 while permitting liquid to flow through the tube 600. The composition of the frit 634 may be the same as or different from that of the tube 600.

Figure 7:
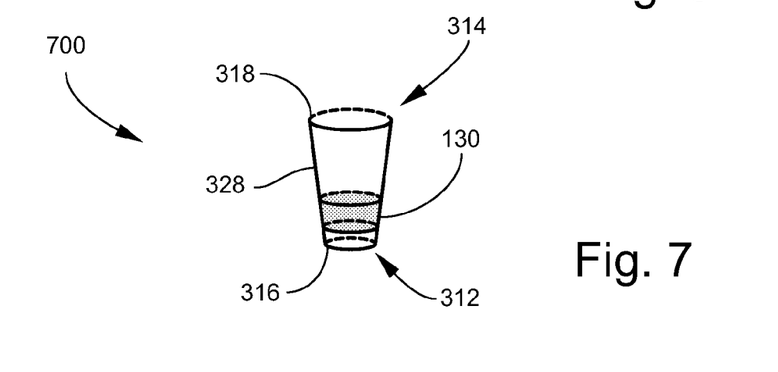
FIG. 7 is an elevation view of another example of a tube extension configured for attachment to the tube illustrated in FIG. 6.

FIG. 7 is an elevation view of another example of a tube extension 700 configured for attachment to the tube 600 in a manner analogous to that described above in conjunction with the tube 100 illustrated in FIG. 1 and the tube extension 300 illustrated in FIG. 3. In the present implementation, the sorbent bed 130 is installed in the tube extension 700 instead of in the tube 600. The tube extension 700 may be axially longer than the tube extension 300 of FIG. 3 to accommodate the sorbent bed 130.

Figure 8:
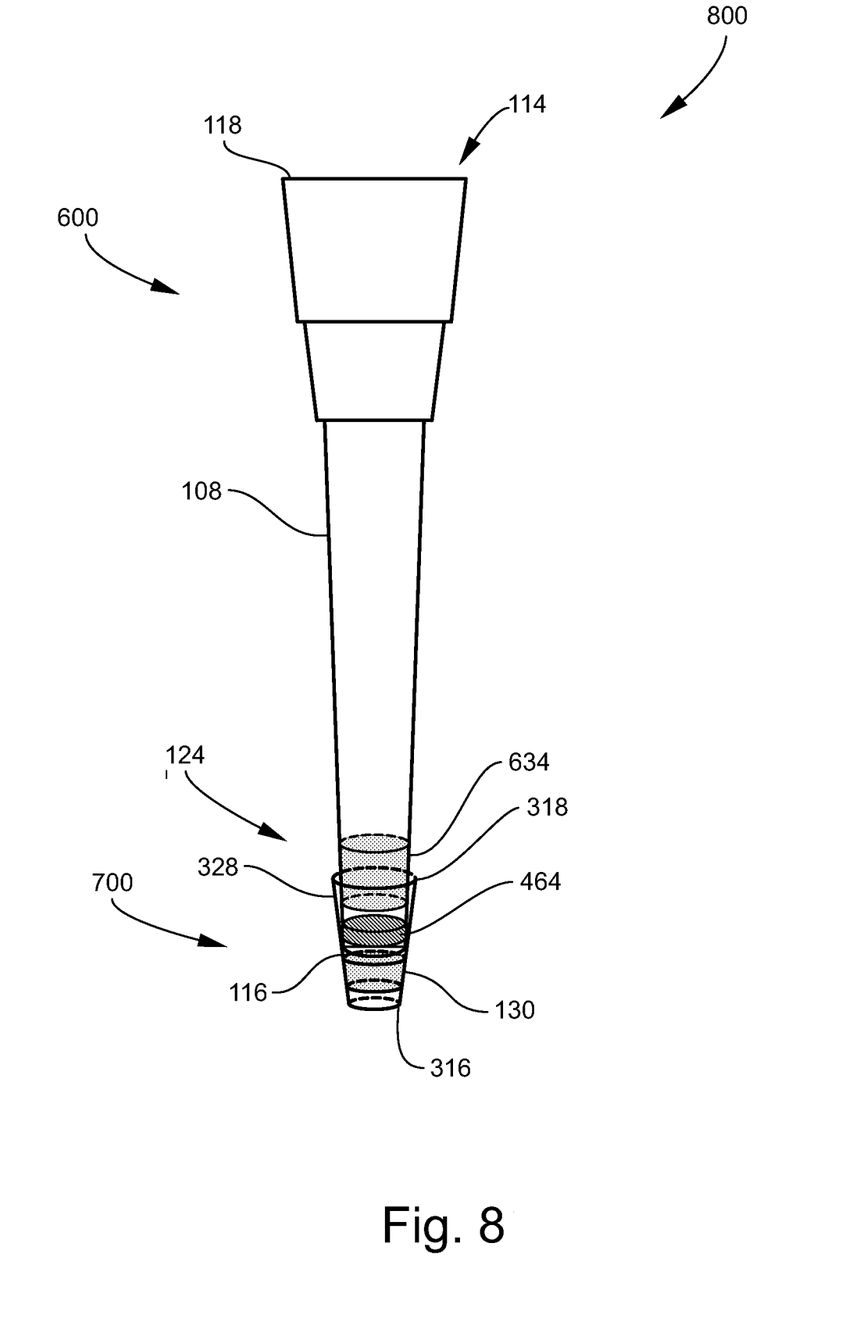
FIG. 8 is an elevation view of another example of an apparatus for punching and extracting analytes from a dried biological fluid spot, including the tube illustrated in FIG. 6 and the tube extension illustrated in FIG. 7 attached to the tube.

FIG. 8 is an elevation view of another example of an apparatus (or device) 800 for punching and extracting analytes from a dried biological fluid spot (or a punch/SPE apparatus). The apparatus 800 includes the tube 600 and the tube extension 700 (with the sorbent bed 130) attached to tube 600.

The apparatus 800 may generally be utilized in any method for acquiring a biological fluid sample in a manner analogous to that of the apparatus 500 described above and illustrated in FIGS. 1-5. According to the implementation, a dried biological fluid sample unit 464 is formed and captured by the tube 600 and the tube extension 700 (with the sorbent bed 130) is then attached in the manner described above. At this point, the sorbent bed 130 may be conditioned as described above, using a conditioning solvent that is weak enough or has a selected composition that conditions the sorbent bed 130 without eluting the sample unit 464. The sorbent bed 130 may also be equilibrated as described above. A first elution solvent (or combination or solvents, with or without buffers or other additives, as needed) is then flowed through the apparatus 800 from the proximal tube opening 118, through the frit 634, around and/or through the sample unit 464, through the distal tube opening 116, through the sorbent bed 130, and through the distal extension opening 316. While the first elution solvent is flowing the sample unit 464 remains captured between the frit 634 and either the distal tube opening 116 or the sorbent bed 130. The flowing solvent causes analytes to be eluted from the sample unit 464 and carried to and retained on the sorbent bed 130. After the analytes are eluted and retained on the sorbent bed 130 in the tube extension 700, the tube extension 700 (with the sorbent bed 130) may be detached from the tube 600 and the sample unit 464 may be removed from the tube 600 by any suitable technique such as, for example, by flowing a wash solvent or other liquid through the tube 600 in the direction of the distal tube opening 116. The tube extension 700 may then be re-attached to the tube 600 and the reassembled apparatus 800 transported to a suitable device for flowing a second elution solvent and forming an analyte-inclusive liquid sample matrix as described above. Alternatively, the tube extension 700 is not re-attached in which case the second elution solvent is flowed only through the tube extension 700 to produce the analyte-inclusive liquid sample matrix. In other implementations as described above, the sorbent bed 130 of the apparatus 800 may be configured for retaining non-analytical material in pass-through clean-up procedures instead of retaining analytes.

In some implementations of the present disclosure, a dried biological fluid punch/SPE kit is provided. The kit may include one or more tubes 100, 600 and one or more plugs of sorbent material, examples of which are described above. In some implementations, the kit may further include one or more tube extensions 300, 700 and/or one or more fits 634, examples of which are described above. The kit may be configured to enable assembly of the apparatus 500 illustrated in FIG. 5, the apparatus 800 illustrated in FIG. 8, or either apparatus 500 or 800, with or without tube extensions 300, 700, at the selection of the user. The tube(s) 100, 600 and tube extension(s) 300, 700 may be disposable, i.e., configured for single-use. In the case of a kit providing two or more tubes 100, 600, the tubes 100, 600 may each have the same dimensions and shape and thus be configured for use in conjunction with a specific type of collection device. Alternatively, the tubes 100, 600 may have different dimensions and/or shapes such that the kit is compatible with more than one type of collection device. Likewise, in the case of a kit providing two or more plugs of sorbent material, the sorbent materials may have the same or different compositions depending on a desired range of applications contemplated for the kit. The kit may provide the frit(s) 634 and sorbent materials separately or preassembled in the corresponding tubes 100, 600 or tube extensions 300, 700. In some implementations, the kit may include tangible media (printed matter, computer-readable storage media, etc.) providing instructions for assembling and utilizing the apparatus 500 or 800 according to one or more methods, etc.

In alternative implementations, the tube 100 may include a filter supported by a frit instead of a sorbent bed. The filter may or may not be configured as a sorbent. Some further examples of a filter and a frit assembled in a tube configured as a punch device are disclosed in U.S. Pat. No. 8,663,580, titled DRIED BIOLOGICAL FLUID SPOT PUNCH DEVICE AND RELATED METHODS, which is incorporated by reference herein in its entirety.

One or more implementations of the apparatus and related methods disclosed herein provide one or more of the following features, advantages, or improvements. The apparatus may be utilized in a wide variety of dried biological sample spot analyses of pharmaceutical compounds, other drug-related compounds, or other chemistries, or high molecular weight (HMW) molecules such as DNA, RNA, proteins or other biopolymers. Such analyses include dried blood spot analyses as noted above. The apparatus provides an effective, reliable technique for punching various types of spot-containing substrates. The apparatus is configured for use with a wide variety of readily available collection devices such a standard multi-well plates, and thus is readily adapted for automated sample extraction/cleanup and analysis. The apparatus is configured for creating liquid sample matrices from dried biological fluid spots by a wide variety of techniques. The apparatus may be fabricated entirely of disposable materials, thereby significantly limiting carryover and cross-contamination.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An apparatus for punching and extracting analytes from a dried biological fluid spot, the apparatus comprising:
   a tube comprising a proximal tube end circumscribing a proximal tube opening, a distal tube end circumscribing a distal tube opening having an inside diameter less than an inside diameter of the proximal tube opening, and a distal section composed of an inert organic polymer having a Rockwell hardness of 89 or greater, the distal section comprising a distal tube wall having a tapered inside diameter that reduces in a direction from the proximal tube end to the distal tube end, the distal tube wall comprising a first section and a second section adjoining the first section and extending to the distal tube end, the first section having a first section thickness and the second section having a second section thickness tapering from the first section thickness to a thickness of the distal tube end less than the first section thickness, wherein the distal tube end comprises a sharp edge; and hardness effective for punching through a substrate on which the dried biological fluid spot is formed such that a sample unit comprising the dried biological fluid spot and a punched portion of the substrate passes through the distal tube opening and is captured in the distal section; and
   a sorbent disposed in the distal section at a distance from the distal tube opening such that the sorbent bed prevents passage of the sample unit to the proximal tube opening, the sorbent bed having a composition configured for solid phase extraction.

2. The apparatus of claim 1, wherein the first section thickness is 0.5 mm or greater and the second section thickness is less than 0.5 mm at the distal tube end.

3. The apparatus of claim 1, wherein the composition of the sorbent bed is selected from the group consisting of an organic polymer, an organic copolymer, an organic polymer blend, a glass fiber cellulose, a metal oxide or metalloid oxide, an ion exchange modified metal oxide or metalloid oxide, a functionalized metal oxide or metalloid oxide, and combinations of two or more of the foregoing.

4. The apparatus of claim 1, wherein the composition of the sorbent bed is configured for retaining analytes from a dried biological fluid spot, or for retaining non-analytical material while passing analytes.

5. The apparatus of claim 1, wherein the distal section comprises an inner shoulder and the sorbent bed is disposed on the inner shoulder.

6. The apparatus of claim 1, comprising a tube extension comprising a proximal extension end circumscribing a proximal extension opening, a distal extension end circumscribing a distal extension opening, and an extension wall having a tapered inside diameter that reduces from the proximal extension opening to the distal extension opening, wherein the proximal extension opening has an inside diameter greater than an outside diameter of the distal end, the distal extension opening has an inside diameter less than the inside diameter of the distal tube opening, and the tube extension is movable between an attached position and a detached position, and wherein:
   at the attached position, the tube extension is secured to the tube by frictional contact between the extension wall and the distal tube end, and the distal extension opening fluidly communicates with the distal tube opening; and
   at the detached position the tube extension is physically separate from the tube.

7. The apparatus of claim 1, wherein the tube has a composition selected from the group consisting of polyolefins, polypropylene, polyethylene, polyamide, polyacrylate, a combination of two of more of the foregoing.

8. An apparatus for punching and extracting analytes from a dried biological fluid spot, the apparatus comprising:
   a tube comprising a proximal tube end circumscribing a proximal tube opening, a distal tube end circumscribing a distal tube opening having an inside diameter less than an inside diameter of the proximal tube opening, and a distal section terminating at the distal tube end, the distal section comprising a distal tube wall having a tapered inside diameter that reduces in a direction from the proximal tube end to the distal tube end, the distal tube wall comprising a first section and a second section adjoining the first section and extending to the distal tube end, the first section having a first section thickness and the second section having a second section thickness tapering from the first section thickness to a thickness of the distal tube end less than the first section thickness, wherein the distal tube end comprises a sharp edge and hardness effective for punching through a substrate on which the dried biological fluid spot is formed such that a sample unit comprising the dried biological fluid spot and a punched portion of the substrate passes though the distal tube opening and is captured in the distal section;

a frit disposed in the distal section at a distance from the distal tube opening such that the frit prevents passage of the sample unit to the proximal tube opening;

a tube extension comprising a proximal extension end circumscribing a proximal extension opening, a distal extension end circumscribing a distal extension opening, and an extension wall having a tapered inside diameter that reduces from the proximal extension opening to the distal extension opening, wherein the proximal extension opening has an inside diameter greater than an outside diameter of the distal tube end, the distal extension opening has an inside diameter less than the inside diameter of the distal tube opening, and the tube extension is movable between an attached position and a detached position, wherein:

at the attached position, the tube extension is secured to the tube by frictional contact between the extension wall and the distal tube end, and the distal extension opening fluidly communicates with the distal tube opening; and at the detached position the tube extension is physically separate from the tube; and a sorbent bed disposed in the tube extension, the sorbent bed having a composition configured for solid phase extraction.

9. The apparatus of claim 8, wherein the frit is fixed in position by frictional contact with the inside tube wall.

\* \* \* \* \*

UNITED STATES PATENT AND TRADEMARK OFFICE
CERTIFICATE OF CORRECTION

Page 1 of 1

PATENT NO. : 9,005,543 B2
APPLICATION NO. : 12/917138
DATED : April 14, 2015
INVENTOR(S) : Robert Lee Grenz et al.

It is certified that error appears in the above-identified patent and that said Letters Patent is hereby corrected as shown below:

Claims

In column 16, line 8, in claim 1, delete "edge;" and insert -- edge --, therefor.

In column 16, line 15, in claim 1, delete "sorbent" and insert -- sorbent bed --, therefor.

In column 16, line 44, in claim 6, delete "end," and insert -- tube end, --, therefor.

In column 17, line 12, in claim 8, delete "though" and insert -- through --, therefor.

Signed and Sealed this
Fourth Day of August, 2015

Michelle K. Lee
*Director of the United States Patent and Trademark Office*